(12) United States Patent
Stafford

(10) Patent No.: US 10,717,023 B1
(45) Date of Patent: Jul. 21, 2020

(54) METHOD FOR CONTINUOUS PURIFICATION

(71) Applicant: Roddy Kevin Stafford

(72) Inventor: Roddy Kevin Stafford, Milford, MA (US)

( * ) Notice: Subject to any disclaimer, the term of this patent is extended or adjusted under 35 U.S.C. 154(b) by 231 days.

(21) Appl. No.: 15/729,669

(22) Filed: Oct. 11, 2017

(51) Int. Cl.
| | |
|---|---|
| *B01J 49/57* | (2017.01) |
| *G01N 1/40* | (2006.01) |
| *B01D 15/38* | (2006.01) |
| *C07K 1/18* | (2006.01) |
| *B01D 15/22* | (2006.01) |
| *C07K 16/00* | (2006.01) |
| *B01D 15/16* | (2006.01) |
| *C07K 1/22* | (2006.01) |

(52) U.S. Cl.
CPC ....... *B01D 15/3809* (2013.01); *B01D 15/168* (2013.01); *B01D 15/22* (2013.01); *B01J 49/57* (2017.01); *C07K 1/18* (2013.01); *C07K 1/22* (2013.01); *C07K 16/00* (2013.01); *G01N 1/405* (2013.01)

(58) Field of Classification Search
USPC ............ 366/50, 150; 436/178; 210/656–657
See application file for complete search history.

(56) References Cited

U.S. PATENT DOCUMENTS

| | | | |
|---|---|---|---|
| 7,988,859 B2 | 8/2011 | Shinkazh | |
| 9,599,594 B2 | 3/2017 | de los Reyes | |
| 2012/0122076 A1* | 5/2012 | Lau | B01D 15/185 435/4 |
| 2013/0184439 A1* | 7/2013 | Spitali | C07K 1/18 530/387.3 |
| 2013/0336957 A1* | 12/2013 | Wang | C07K 16/00 424/130.1 |
| 2014/0154270 A1* | 6/2014 | Wang | B01D 15/3809 424/177.1 |
| 2014/0288278 A1* | 9/2014 | Nti-gyabaah | B01D 15/3809 530/388.24 |

(Continued)

FOREIGN PATENT DOCUMENTS

WO    WO 2012/031008 A3    3/2012

OTHER PUBLICATIONS

Ettre,L.S. "Nomenclature for Chromatography", International Union of Pure and Applied Chemistry, Pure & Appl. Chem., 1993, 819-872, vol. 65, No. 4.

(Continued)

*Primary Examiner* — Nina Bhat
(74) *Attorney, Agent, or Firm* — Shirley A. Recipon

(57) ABSTRACT

A device and method for the separation of a compound or compounds from impurities is described. The device comprises a tube having a mixing apparatus that mixes by convection a feedstock comprising one or more products such that the products can be bound to a resin and then contacted with various buffer solutions. At various distances along the cylindrical module, solutions (e.g., sample products to be purified, buffers, etc.) of various compositions can be sequentially added and removed. The resin particles can be retained within the module by filters or screens at the addition and exit ports. In this way, a slurry of resin particles can be continuously equilibrated, loaded with product, washed of impurities, eluted of processed product(s), stripped, re-equilibrated and recycled for re-use.

18 Claims, 9 Drawing Sheets

(56) References Cited

U.S. PATENT DOCUMENTS

| | | | |
|---|---|---|---|
| 2015/0110799 A1* | 4/2015 | Ramasubramanyan | ........................ C07K 16/241 424/142.1 |
| 2015/0110803 A1* | 4/2015 | Wang | ................... C07K 16/241 424/158.1 |
| 2016/0367911 A1* | 12/2016 | Carredano | ........... B01D 15/362 |
| 2018/0009876 A1* | 1/2018 | Yonan | .................... C07K 1/165 |

OTHER PUBLICATIONS

Girard, Valerie et al., "Large-scale monoclonal antibdy purificiation by continuous chromatography, from process design to scale-up", Journal of Biotechnology,May 8, 2015, 65-73, vol. 213.

Hober, Sophia et a., "Protein A chromatography for antibody purification", Journal of Chromatography B, Oct. 9, 2007, 40-47, 848.

Jansson, Birger, et al., "All individual domains of staphylococcal protein A show Fab binding", FEMS Immunol. Med. Microbiol.,1998, 69-78, 20.

Kulsing, Chadin, et al., "Insights into the Origin of the Separation Selectivity with Silica Hydride Adsorbents", J. Phys. Chem. B, Feb. 6, 2015, 3063-3069, 119.

Low, Donald W., et al., "Total synthesis of cytochrome b562 by native chemical ligation using a removable auxiliary", PNAS, Jun. 5, 2001, 6554-6559, vol. 98, No. 12.

Martin, A.J.P. and R.L.M. Synge, "Some applications of periodic acid to the study of the hydroxyamino-acids of protein hydrolysates", Biochem. J. Mar. 1941, 294-314.1., 35(3).

Martin, A.J.P. and R.L.M. Synge, "A new form of chromatogram employing two liquid phases, 1. A theory of chromatography. 2. Application to the micro-determination of the higher monoamino-acids in proteins", Biochem J. Dec. 1941, 1358-1368, 35(12).

Muller, J.H. and Matthias Franzreb, "Suitability of commercial hydrophobic interaction sorbents for temperature-controlled protein liquid chromatography under low salt conditions", J. Chromatography A, Aug. 23, 2012, 88-96, 1260.

Ren, Jun, et al., "Salt-independent hydrophobic displacement chromatography forantibody purification using cyclodextrin as supermolecular displacer" J. Chromatography A, Oct. 12, 2014, 98-104, 1369.

Singh, Naveen Kumar, "Direct CApture of His6-Tagged Proteins Using Megaporous Cryogels Developed for Metal-Ion Affinity Chromatography", Senta Reichelt (ed.), Affinity Chromatography: Methods and Protocols, Methods in Molecular Biology, Mar. 2015, 201-212, vol. 1286.

Botti, Paolo, et al., "Native chemical ligation using removable Nalpha-(1-phenyl-2-mercaptoethyl) auxiliaries", Tetrahedron Letters 2001, 1831-1833, 42.

Dutta, Amit K., et al., "Performance optimization of continuous countercurrent tangential chromatography for antibody capture", Biotechnol. Prog., Mar. 17, 2016, 430-439, 32(2).

Gaberc-Porekar, Vladka and Viktor Menart, "Perspectives of immobilized-metal affinity chromatography", J. Biochem. Biophys. Methods, 2001, 335-360, 49.

Ghose, Sanchayita, et al., "Binding Capacity Differences for Antibodies and Fc-Fusion Proteins on Protein A Chromatographic Materials", Biotechnology and Bioengineering, Jul. 1, 2006, 768-779, 96(4).

Goding, James W., "Use of Staphylococcal Protein A as an Immunological Reagent", J. Immunol. Meth., 1978, 241-253, 20.

Hostettmann, K., et al., "Preparative Chromatography Techniques", 1986, pp. 41, 46-51, Springer-Verlag, Berlin, GDR.

Stafford, Kevin, "True Moving Bed Chromatography (Tmbc)", J. Biotechnology and Bioengineering, 2019, 12-16, 3(3).

* cited by examiner

METHOD FOR CONTINUOUS PURIFICATION

This application claims priority to U.S. Provisional Application No. 62/496,161, filed Oct. 11, 2016. Application Ser. No. 62/496,161 is incorporated by reference herein in its entirety for any purpose.

FIELD

The present teachings generally relate to the separation, purification and formulation/buffer exchange of compounds including, but not limited to, proteins, foods, nutraceuticals, organic acids, and vitamins, from impure mixtures. More specifically, the disclosed invention relates to a device, method and system, using chromatographic resins, to purify compounds and products including, but not limited to, biotherapeutic proteins, biologics, antibodies, extract bulk biochemicals from impurities, and to isolate protein factors and fractions, all of which are used in a variety of applications.

BACKGROUND

The disclosed device, method and system can be useful for purifying a number of types of products from impurities. These can include biotherapeutic proteins and bulk biochemicals. The potential market of such products exceeds $2,000,000,000 annually. The disclosed device provides a substantial reduction in manufacturing costs of such products.

Column chromatography was described by Martin and Synge in 1941. Column chromatography is the current state of the art for purifying proteins from complex mixtures. Apart from affinity chromatography (Goding J W J. (1978), there has been little innovation in the field since its introduction.

Upstream technologies for protein production has improved product yields with the development of systems that utilize plant cells, bacterial cells, insect cells, and mammalian cells having high level expression systems and growing to high cell densities. Mammalian cell culture bioreactors have greatly increased (up to 20,000 liters) and the titers are much higher today than they were in the past. Because of larger volumes, longer fermentation times, and higher cell densities, the amounts of product and associated impurities are generally greater in the bioreactor culture fluid than in the past. Thus, improvements in product separation and purification are needed. Improvements in classical chromatography devices, methods and systems are disclosed to address this need.

Column chromatography, as traditionally practiced, utilizes an insoluble resin particle (e.g., a solid matrix particle) coated with a product binding ligand that is added to a tube (column) and allowed to settle into a "packed bed". A suitable buffer is then pumped through the bed allowing equilibration of the ligands, to allow them to bind the desired product. The solution containing the crude product, the load, is then pumped through the resin bed. The product binds to the resin ligand along with some impurities. Another buffer, the wash buffer, formulated to wash away lightly binding impurities from the product is pumped through the resin bed and discarded. This is followed by an elution buffer, a buffer that allows the product to detach from the resin ligands, is then pumped though the resin bed and the product is eluted and collected. A buffer that detaches tightly bound impurities, the strip buffer, is then pumped through the resin bed detaching any tightly binding impurities from the resin and collected as waste. Finally, a buffer that has been formulated to re-equilibrate the resin is pumped though the resin bed enabling the entire process to be repeated.

It can be understood from the preceding description that column chromatography contains inherent limitations for purification. It is labor intensive in part because it is operated one step at a time in a batchwise process. In addition, the amount of product that can be processed depends on the size of the packed bed. Also, the rate at which material is produced depends on the maximum buffer flow rate through the packed bed. The restriction of the buffer flow rate by the packed bed causes the pressure to increase as the buffer flow rate increases. The decrease in flow rate increases process time and can adversely impact process productivity.

Column chromatography also has inherent physical limitations due to the size of the chromatography column. Chromatography columns larger than one meter in diameter are very difficult to prepare. The largest columns on the market are two meters in diameter and forty centimeters high. With these dimensions, the column can accommodate 1,250 L of resin. Since the cost of protein A resin is approximately $10,000/L, the cost of a 1,250 L protein A column is exorbitant. And assuming a binding capacity of 30 g of product/L of resin (common protein A resin capacity for monoclonal antibodies), and a chromatography column with a 50 L volume, can, in a single cycle, only bind 1.5 kg of product. A 2,000 L bioreactor with an output of 10 g/L would require a column load capacity of 200 kg. This means that the 50 L column would have to run at least 13 full cycles to process a single batch of processed protein product. Such an operation can take several days and can result in a significant production bottleneck for the manufacturing process.

Therefore, it was recognized by the inventor that breakthrough innovations in the state of the art could include 1) increased scale—leading to a larger scale of operation; 2) faster processing time; 3) reduction of raw material costs; and 4) a reduction of capital equipment costs enabled by continuous process technology.

The disclosed invention advances purification methodologies of processed products and the applications for methods derived from chromatography devices significantly by enabling continuous separation, and/or purification and/or formulation while reducing manufacturing costs and process complexity for a wide range of product types including, but not limited to biotherapeutic proteins, biologics, pharmaceuticals, antibodies and isolation of blood components, protein factors and protein fractions as well as bulk biochemicals from their natural sources. The disclosed invention can be used to replace existing slow, inefficient, batchwise processing methods with modern continuous manufacturing technology controlled by PAT (process analytical technology). Therefore, the disclosed device, methods and systems meet the need of providing easier, faster and more economical product processing technology.

BRIEF SUMMARY OF THE INVENTION

Disclosed are devices, methods of producing products and systems for economical and efficient purification of products. The disclose devices can affect separation, purification and formulation/buffer exchange of compounds including, but not limited to, proteins, foods, nutraceuticals, organic acids, and vitamins, from impure mixtures. The disclosed embodiments provide features and aspects of the disclosed inventions.

In one embodiment, disclosed is a device, having a cylindrical module comprising one or more mixing apparatus within the cylindrical module, an input port for loading a resin within the cylindrical module, one or more air bleed valve(s), wherein the valve extracts accumulated air within the module, one or more first port(s) for adding a sample load solution and one or more first exit port(s) for removing sample load waste solution essentially absent sample, optionally, one or more second port(s) for addition of a wash solution and one or more second exit port(s), for removal of wash solution essentially absent sample, at least one or more elution solution port(s) for addition of an elution solution and at least one or more elution exit port(s) for recovery of the elution solution containing a processed sample, optionally, one or more additional port(s) for addition of a solution and of one or more additional exit port(s) for removal of the solution, wherein said ports can be used during a single pass through the device at least one or more times to repeat one or both of steps d) and e), wherein the sample load solution comprises two or more samples to be processed, and a system for recycling the resin contained within the module having: at least one or more port(s) for addition of a strip solution and at least one or more exit port(s) for removal of the strip solution, wherein sample impurities bound to the resin are removed, at least one or more port(s) for addition of resin equilibration buffer, wherein stripped resin is re-equilibrated, at least one or more exit port(s) for removing >10% equilibration buffer, and at least one or more exit port(s) for removing re-equilibrated resin, wherein the exit port(s) is in communication with a tubing, and one or more pumps interconnect to the tubing containing re-equilibrated resin, wherein re-equilibrated resin is recycled into the cylindrical module.

In one embodiment, the disclosed device loads the sample solution that can be adjusted in conductivity and/or pH, in which impurities within the sample load solution do not bind to the resin and are removed through the one or more first exit ports. In another embodiment, the mixing apparatus promotes convective mass transfer between the sample load solution and the resin. The convective mass transfer can be achieved by adjusting the mixing apparatus by at least one parameter selected from the group consisting of higher RPMs, increase in cylindrical module diameter, increasing one or more of sample load solution, wash solution and/or elution solution flow rates, mechanical projections within the mixing apparatus and combinations thereof.

In one embodiment, the device can optionally have one or more analytical instruments.

In one embodiment, the resin used within the device can be selected from the group consisting of an anion exchange resin, a cation exchange resin, an affinity resin, a hydrophobic interaction resin, and a reverse phase resin. In addition, the device can optionally have a resin injection port. In another embodiment the device can have a pump at each addition port and exit port.

In one embodiment, the disclosed device can be used in a method for producing a processed product comprising: applying a sample load solution comprising one or more product(s) plus impurities to the disclosed device via one or more first port(s), wherein product binds to resin, and removing sample load waste solution via one or more first exit port(s), essentially absent sample, optionally, applying a wash solution via one or more second ports, wherein impurities from the sample solution can be removed in wash solution via one or more second exit ports, essentially absent sample, and applying an elution solution to elute product bound to resin via one or more elution ports, wherein the product can be a processed product collected via one or more elution exit ports. The processed product can be selected from the group consisting of a separated product, a purified product, and formulation/buffer exchange of compounds, and combinations thereof.

In one embodiment, disclosed is a method of producing two or more products from a single feed stock comprising: applying a sample load solution comprising impurities and two or more products to be processed to the device of claim 1 via one or more first port(s), wherein two or more products substantially bind to resin and removing sample load solution via one or more first exit port(s), essentially absent sample, optionally, applying a wash solution via one or more second port(s), wherein impurities can be removed via one or more second exit port(s), essentially absent sample, applying a first elution solution via one or more first elution port(s), wherein a first processed product is eluted from the resin and collected via one or more first elution exit port(s), optionally, repeating step b) before repeating step c) via at least one or more optional wash port(s) and adding a second wash solution to one or more second wash port(s).

In another embodiment, the elution of additional processed product(s) can be carried out via one or more additional elution port(s) wherein a second and each additional processed product can be eluted from the resin and collected via one or more additional elution exit port(s) for recovery of the second and each additional processed product(s). In yet another embodiment, the feedstock can be selected from the group consisting of a compound product sample and a blood product. The blood product can be plasma and recovered from the plasma can be at least two proteins selected from coagulation factor(s), plasma protein fraction(s), and combinations thereof.

In one embodiment, disclosed is a method of processing an analyte comprising: applying a crude sample solution comprising an analyte plus impurities to the device of having one or more analytical instruments, via one or more first port(s), wherein analyte binds to resin, and removing crude sample solution via one or more first exit port(s), essentially absent sample, optionally, applying a wash solution to wash analyte bound to resin via one or more second ports, wherein impurities from the crude sample solution can be removed via one or more second exit port(s), essentially absent sample, applying an elution solution to elute the analyte from resin via one or more elution ports, wherein processed analyte is collected via one or more elution exit ports, analyzing the processed analyte for purity, and optionally quantifying the analyte, and the analyte can be a processed analyte.

In yet another embodiment, the analysis can have process analytical technology (PAT). PAT provides feedback for adjusting a processing parameter selected from the group consisting of: mixing apparatus speed, pump flow rates selected from the group consisting of sample load solution, processing solution buffer, resin injection and resin recycle. Such a feedback can assist with efficient and economical analyte and product processing in a continue processing system such as the disclosed device.

This summary is intended to provide an overview of subject matter of the present patent application. It is not intended to provide an exclusive or exhaustive explanation of the disclosed invention. The detailed description is included to provide further information about the present patent application.

BRIEF DESCRIPTION OF THE DRAWINGS

An understanding of the features and innovations of the present disclosure will be realized by reference to the accompanying drawings. It will be appreciated that for simplicity and clarity of illustration, elements illustrated in the Figures are not necessarily drawn to scale and elements may function within the device other than as illustrated. For example, the dimensions of some elements may be exaggerated relative to other elements. The drawings are intended to illustrate, not limit, the present teachings. Embodiments incorporating teachings of the present disclosure can be shown and described with respect to the drawings herein, in which.

The figures are schematic and simplified for clarity, and show details to further understanding of the disclosure, while other details are left out. Throughout, the same reference numerals are used for identical or corresponding parts.

DETAILED DESCRIPTION OF VARIOUS EMBODIMENTS

Figure 1:
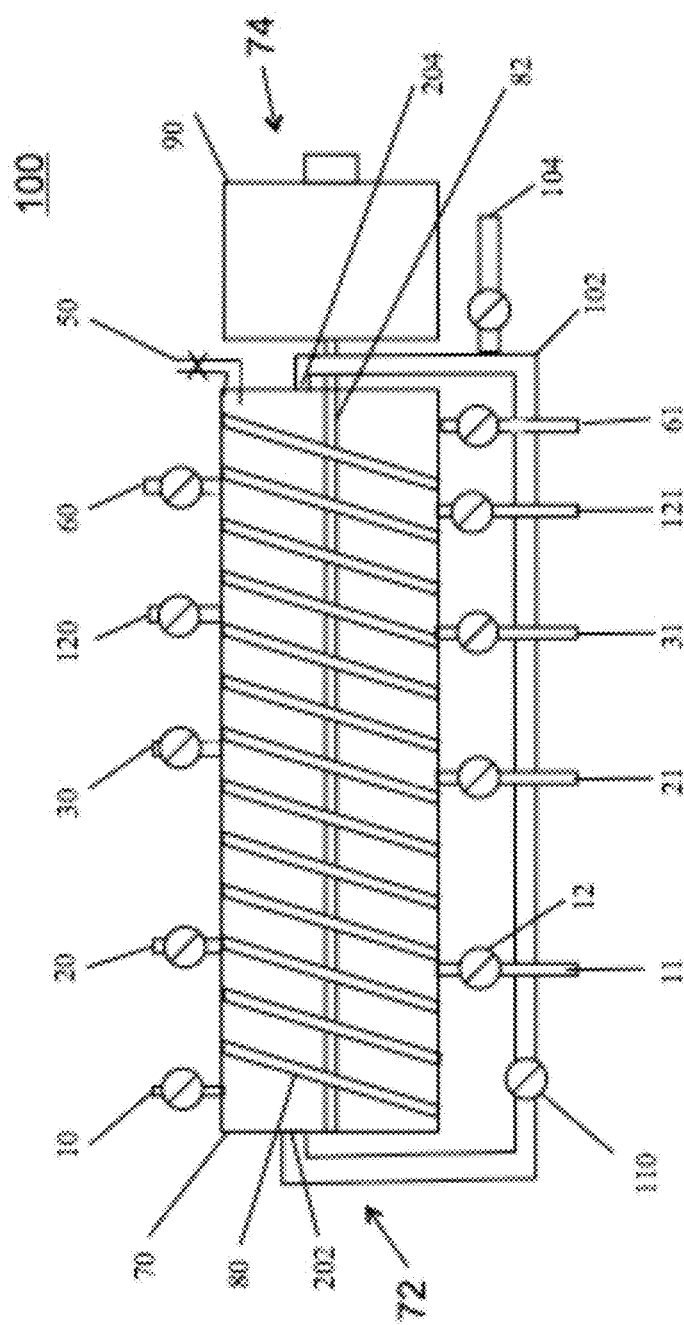
FIG. 1 is a schematic view of one embodiment of the disclosed device.

Before the devices and methods of the present disclosure are described, it is to be understood that the invention or inventions disclosed herein are not limited to the particular devices, processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred devices, method sand materials are now described. Nothing herein is to be construed as an admission that the invention or inventions disclosed herein are not entitled to antedate such disclosure by virtue of prior invention.

As used herein, the singular forms "a," "an," and "the" include plural reference unless the context clearly dictates otherwise. Thus, for example, reference to a "pump" is a reference to one or more pumps and equivalents thereof known to those skilled in the art, and so forth.

As used herein, the term "about" means plus or minus 5% of the numerical value of the number with which it is being used. Therefore, about 20% means in the range of 19% to 21%.

The following terms of art shall have the below ascribed meanings throughout this Specification.

The term "resin" as used herein can describe an insoluble particle matrix that functions in one or more of a separation, purification and formulation/buffer exchange process, either simultaneously or successively. The particles can be composed of a resin or polymer, including but not limited to polystyrene sulfonate, cross-linked polystyrene, chelating resins, etc. as is known to one of skill in the art. The particles can be solid, porous, increasing the surface area both externally and internally and/or coated with a ligand that can be capable of reversibly binding a desired product, impurity and combinations thereof.

The terms "feedstock," "bioreactor supernatant," "sample buffer," "sample load buffer," "biological fluid," and "sample" can be used interchangeably and can refer to the source material solution having the desired product(s) to be recovered from the source solution by the disclosed device, and methods of using the device to produce the desired product(s). The source of the sample can include, but is not limited to, a cell culture supernatant, a cell fermentation supernatant, a recombinant cell culture supernatant, a recombinant cell fermentation supernatant, a plant extract, a cell culture extract, and a cell fermentation extract.

The term "loading" as used herein can describe a stage of operation of the disclosed devise during which an insoluble particle matrix (resin) and unprocessed product, product to be separated, product to be purified, and product with one or more factions to be separated and processed, can be bound together to form a reversible complex. The term "Load" as used herein can refer to a feedstock or sample load solution or crude sample solution having an analyte, comprising the compound/product to be separated and/or purified from the feedstock.

The term "sample buffer" as used herein can describe the medium, including but not limited to a bioreactor supernatant, fermentation tank supernatant, and biological fluid, to which desired product(s), can be bound during the process of purification, isolation or separation. The resin having bound to it, the desired product to be purified, moves/carries the desired product along the length of the cylindrical module(s) during the purification, isolation or separation processes.

The term "processed product" as used herein can describe a product recovered from a sample buffer. The product has been separated, purified or isolated from impurities associated with the sample buffer comprising the desired product(s).

The term "purification" as used herein can describe the continuous separation of a desired product, compound, factor or fraction from impurities via co-current extraction chromatography.

The term "washing" as used herein can describe a stage of operation during which a resin with bound product can be washed with a buffer to rid the resin/product matrix of impurities while retaining bound product.

The term "elution" as used herein can describe an operation during which the product can be eluted from the resin and the processed product can be collected.

The term "strip" as used herein can describe a stage of operation during which the resin can be cleaned, e.g., product impurities bound to the resin can be removed, for the purpose of reuse of the resin or for use in later cycles as would be understood by the skilled artisan.

The term "equilibration" as used herein can describe a stage of operation during which the resin can be placed in a form that allows product to bind reversibly to the product. For example, most proteins can be put into a suitably ionized state to bind due to ionic charge. In anther example, an antibody, the antibody protein is not in an altered ionic state. Rather, with respect to antibodies, including but not limited to, a monoclonal antibody, the affinity ligand will bind the monoclonal antibody protein product based on the monoclonal antibodies native conformation.

The term "residence time" as used herein, can be a calculated parameter describing the amount of time either the buffer or resin spend in any portion/area/region of the device. It can be calculated by dividing the module volume through which the resin flows by the flow rate in volume per time. The dimension can be expressed as units of time.

What is disclosed herein are embodiments of a device containing a cylindrical module having one or more mixing apparatus within the module and traversing up to the length of the module. The module can be filed with a solid support matrix, including but not limited to a chromatography resin for purification of products, including, but not limited to, biotherapeutic proteins, biologics, antibodies, extracting bulk biochemicals from their natural sources and to isolate protein factors and protein fractions.

In another embodiment, the disclosed device, methods of producing product(s) with the device and systems using or within the device's operation can find application and use in a variety of fields. Fields include but are not limited to human health care, disease diagnosis, preparation as well as manufacture of biotherapeutics, including but not limited to biologics, pharmaceuticals, homeopathic materials and biochemicals. Additionally, the fields of Forensics, Veterinary Medicine, Agriculture and Research into any of the listed fields can find processed product improvements using the disclosed device methods and systems.

Reference will now be made to various embodiments, examples of which are illustrated in the accompanying drawings.

The present invention relates to the separation of a compound or compounds from impurities using insoluble particles (resin) containing a ligand that binds the compound of interest reversibly. The insoluble particles can be contacted by buffers of appropriate compositions that enable equilibration, binding, washing, elution, and stripping of the resin in preparation for re-equilibration. The resin can be recycled for re-use. In a preferred embodiment, the resin can be passed through a cylindrical module, contacting various buffers, and continuously recycled to the proximal end for reuse. At appropriate distances/zones along the pipe, solutions of various compositions can be sequentially added and removed. The rotation of the mixer can be adjusted to provide adequate contact time of the resin and each solution. The resin particles can be retained in the module by filters or screens at the solution exits. In this way, a slurry of resin particles can be continuously equilibrated, loaded, washed, bind, eluted, stripped and recycled for re-use.

For a given volume of crude process fluid to be processed, substantial benefits can be realized over conventional column chromatography, including reduced resin requirements owing to the recycling of the resin, reduced buffer requirements owing to improved convective mixing of buffer with resin, and higher processing rates due to higher fluid flow rates enabled by lower backpressures than in conventional column chromatography. Also, the residence time of the resin and the residence time of the buffer can be independently controlled allowing optimization of the system providing improved efficiency, rate of processing and product recovery.

The disclosed innovation can more easily implement process analytical technology (PAT) enabling real time control of buffer flow rates and mixing (e.g., helical screw rotation) rate. The use of on-line monitors that allows real-time computer or operator control of buffer feed pumps and the mixing (e.g., screw drive revolution) rate, can be more easily implemented. Additionally, analytical instruments such as conductivity probes, pH probes, and absorbance probes, can analyze the exiting buffers and provide automated feedback to an operator or a computer that controls the buffer pumps and resin transport mechanism to optimize the operation of the device in real time.

Several versions of the disclosed device, as depicted in FIG. 1 and FIGS. 3-8 can be envisaged by one skilled in the art. The device and system can also be configured as an analytical device. If the device would be fitted with an appropriate analyzer, the eluted product stream can be analyzed for product quantity, purity and impurity content.

In one embodiment, the device has a cylindrical module with an integrated mixing apparatus for aiding the binding of the sample (e.g., product) to the resin slurry disposed within the module. The module has numerous inlet and outlet ports. Input and outlet ports for buffer in and waste buffer out can be arranged around the circumference at discrete intervals to allow binding, washing and elution of sample at each interval. The disclosed device has the advantages of: 1) scalability—leading to a larger scale of operation; 2) faster processing time; 3) reduction of media/resin volume and expenses; and 4) a reduction of capital equipment investment enabled by continuous process technology.

The continuous processing/movement of the resin slurry precludes issues of resin packing making operation at a larger scale simpler. Additionally, continuous movement of the resin slurry having product bound minimizes pressure build-up within the module resulting in more consistency of flow rate within the module. Uniquely, the ability to recycle the resin at the distal end of the module, following elution of the recovered product, and pump the equilibrated resin back into the proximal end of the module significantly reduces resin expenditure, prolongs resin lifecycle and can necessitate a smaller volume of resin/total product recovered compared to traditional column chromatography methodologies. The improved efficiency in processing using a smaller industrial footprint due to substantial reductions in module diameters, and binding of product results in improved product recovered per volume per unit time. These improvements when combined with a continuous process workflow lowers the overall capital equipment investment to reduce the cost/product unit produced.

To illustrate one embodiment, FIG. 1 illustrates disclosed device 100. Equilibrated resin, as a slurry, flows into a cylindrical module 70 at the proximal end 72 containing a mixing apparatus 80 (a helical screw is presented for illustration purposes only and is not intended to be limiting) and can be moved down the longitudinal axis by screw 80 rotation controlled by the variable speed drive 90. Product with associated impurities can be added by one or more of port 10. The one or more port 10 inlet(s) can be within a plane and around the circumference of module 70. Any impurities that do not bind to the resin can be removed by gravity or a pump 12 at the waste exit port 11. As with the inlet port 10, there can be one or more of waste exit port(s) 11. The one or more port 11 exit(s) can be within a plane and positioned around the circumference of module 70. A wash buffer formulated to remove weakly binding impurities without removing product can be added at one or more of input port(s) 20. Wash buffer containing impurities can be removed at one or more port(s) 21. Just as with the one or more inlet ports 10 and one or more waste outlet ports 11, each of the one or more ports 20 and 21 can each be within a plane and positioned around the circumference of module 70. An elution buffer formulated to elute the product from the resin, can be added at one or more of inlet port(s) 30. Elution buffer containing the processed product can be recovered and removed at one or more of port(s) 31. Just as with the one or more inlet ports 10 and one or more waste outlet ports 11, each of the one or more ports 30 and 31 can each be within a plane and dispersed around the circumference of module 70. A Strip buffer, formulated to remove from the resin strongly binding impurities, can be introduced at inlet port(s) 120 and removed at outlet port(s) 121. Just as with the one or more inlet ports 10 and one or more waste outlet ports 11, each of the one or more ports 120 and 121 can each be within a plane and dispersed around the circumference of module 70. A resin Equilibration Buffer can be introduced at one or more of port(s) 60 and removed at one or more of port(s) 61. After equilibration of the resin it can be removed from module 70 at port 204 in communication with recirculation tube 102 positioned at distal end 74 of module 70 and can be mixed with additional resin added at port 104. Equilibrated resin can be pumped back to the resin recycle entrance 202 by pump 110 through recirculation tube 102 in direct communication with re-equilibrated resin exit port 204. Cylindrical module 70 can have at least one air bleed valve 50 to removal of air from within the module. Each of the inlet and outlet ports has a pump 12, as illustrated in FIG. 1, though only two of pumps 12 are labeled.

The planar arrangement of the inlet and outlet ports can be illustrated in top-down view 200 of the proximal end 72 of FIG. 1. The resin return entrance 202 can replenish resin within cylindrical module 70. Mixing apparatus (e.g., a helical screw) 80 revolves around its center shaft 82. Four load inlet ports 10 can be depicted as four load waste outlet orts 11. The arrangement of the inlet ports around the circumference of module 70 in one plane and a separate plane having the outlet ports around the circumference of module 70 is illustrated.

In another embodiment, the disclosed device can be used to change the buffer of the product. Often replacing buffer of a product with another buffer can be performed. This process can be sometimes performed using membranes in a process referred to as ultrafiltration/diafiltration (UF/DF). However, UF/DF cannot be used effectively in situations where one of the components of the original buffer contains a component that can be rejected by the membrane, for example polysorbate. In such cases, a column based buffer exchange can be performed, also referred to as "on-column buffer exchange". In on-column buffer exchange the product can be bound to the resin and the original buffer flows though the column. A second buffer would then be pumped through the column and the product would be eluted.

In another embodiment, the mixing apparatus, including but not limited to a helical screw, at least one static mixer and other convective mixing devices and methodologies as is known to the skilled artisan can be modified to improve convective mixing and thus efficiency of buffer contact with the resin. By increasing the number of turns per meter, and increasing the rpm of the drive 90, the velocity of resin passing though the buffer can be increased. Additionally, increasing the number of screw channels per meter of the screw effects linear velocity (mm/min) of the resin though the buffer that can increase convective mass transfer at a constant residence time. as shown below in Table 1:

TABLE 1

| OD Diameter of Screw, mm | Number of channels | RPM of screw | Residence Time of Resin, min | Linear Velocity at perimeter, mm/min |
| --- | --- | --- | --- | --- |
| 25.4 | 1 | 10 | 0.1 min | 800 |
| 25.4 | 5 | 50 | 0.1 min | 3989 |
| 25.4 | 10 | 100 | 0.1 min | 7978 |

In another embodiment, the diameter of the screw can be increased to increase convective mass transfer, to bind together the resin and the buffer. In another embodiment, the screw can be designed to increase turbulence as it turns by adding protrusions in the channels of the screw. The effect of screw diameter on linear velocity is shown in Table 2.

TABLE 2

| OD Diameter of Screw, mm | Number of channels | RPM of screw | Residence Time of Resin, min | Linear Velocity, mm/min |
| --- | --- | --- | --- | --- |
| 25.4 | 1 | 10 | 1 | 800 |
| 50.8 | 1 | 10 | 1 | 1596 |
| 110.6 | 1 | 10 | 1 | 3191 |

The capability of a chromatography column to resolve one protein from another is intrinsically limited as described by the VanDeemter Equation 1 used to describe the resolution of proteins on a chromatography column.

Height Equivalent to a Theoretical Plate (HETP)=$A+B/u+((C_{mobile}+C_{stationary})\times u)$   Equation 1:

Where:
A is the increase in plate height (cm) due to inhomogeneity of the packed bed
B is the increase in plate height (cm2/sec) due to diffusion of the product
$C_{mobile}$ is the mass transfer resistance (sec) of the mobile phase
$C_{stationary}$ is the mass transfer resistance (sec) of the stationary phase
u is the flow rate(cm/sec) of the buffer The VanDeemter equation describes the variables that affect the HETP of chromatography columns. This relationship shows that the HETP is the sum of three terms, A which is proportional to inhomogeneities of packing in the resin bed, B/u which is proportional to product diffusion ahead of and behind the buffer front, and the sum of the resistances to mass transfer of the product to the stationary phase and the mobile phase to the resin. The disclosed device dramatically reduces the first two terms and has a significant impact on the third resulting in sharper peaks and greater resolution of one product from another.

In another embodiment, the conductivity of the load can be adjusted to prevent impurities from binding to the resin thus allowing them to flow through the resin to waste. If the product can be eluted at 30 mSm/cm for example, the load can be adjusted to 29 mSm/cm preventing impurities from binding during the load step, allowing them to flow through the device to waste. This modification eliminates the need for a separate wash step and increases the rate of processing as well as eliminating one process buffer.

The conductivity of the elution buffer can be a characteristic that affects the binding and elution of the processed protein and resin. Adjusting conductivity to a value that displaces (i.e., elutes) the processed protein from the resin can result in the protein eluting from the resin. Resolution of one protein from another can be mediated by use of a packed bed. As the conductivity reaches a critical point and as proteins travel down the resin bed, they can be attracted to the resin, and can be released from the resin based on an interaction between their net charge and the conductivity of the buffer. This differential attraction causes proteins to migrate at slightly different rates and the proteins resolve from one another.

In contrast, in column chromatography, proteins are in a dynamic state of attraction and release. They are only fully attached to resin at a particular conductivity. This causes "banding" of various proteins and the resultant peaks. Thus, as the bed depth increases, resolution decreases due to diffusion of the product ahead of and behind the buffer front and mass transfer differences due to resin bed inhomogeneity.

Alternatively, the disclosed device can resolve one protein from another absent adverse effects presented by inhomogeneities of a resin bed and the resulting peak spreading of the product due to diffusion. While not wishing to be bound by a particular theory, the disclosed devise can resolve one protein from another potentially due to differences in net charges of the proteins to be separated at different conductivities. In addition, the resistance to mass transfer as described by the VanDeemter equation can be reduced by its third term, resistance to mass transfer ($C_{mobile}$). In contrast, mixing in a conventional column can be dominated by diffusion. In the disclosed device, mixing can be dominated by convection. For these three reasons the disclosed device results in greater resolution and so separation of one protein from another. Thus, the disclosed device will operate faster and increase product resolution, and therefore, product purity.

Furthermore, conventional column chromatography can be a batch operation, a column can be scaled such that it can be capable of processing the maximum amount of load based on the dynamic binding capacity of the resin. The buffer flow rates can be adjusted to their maximal values without exceeding the pressure that crushes the resin or exceeds the pressure specifications of the equipment. This method of process scale-up can be inefficient in that it requires more resin and slower flow rates than would be necessary with the disclosed device.

The disclosed device's operation differs from conventional column chromatography in two ways. First, the difference in the method of resin utilization. This can be demonstrated by the reduction of resin used by the disclosed device due toe resin recycling and highlights the reduction in the cost of expensive resins such as Protein A ($10,000/L). Second, the device can operate with shorter cycle times at constant resin utilization resulting in increased productivity.

Table 3 compares the parameters of a conventional chromatography column with those of the disclosed device on two bases, 1) reduced resin utilization and 2) reduced cycle time. The basis of comparison can be the purification of a 2000 L bioreactor at 1 g/L (total of 2 Kg). The disclosed device, utilizing just 10% of the resin can be capable of processing all of the product in less time (2 hours) than a conventional chromatography column (3 hours). A 50 L volume of a Protein S or Protein A resin would cost $250,000 for the conventional column and only $25,000 for the disclosed device.

TABLE 3

Resin Requirements of Conventional vs. Disclosed Device

| Resin | Conventional 100% Resin SP Sepharose Fast Flow | Disclosed Device 10% Resin Use SP Sepharose Fast Flow | Disclosed Device Reduced Cycle Time SP Sepharose Fast Flow |
|---|---|---|---|
| Height (cm) | 45 cm | 18 cm | 45 cm |
| Diameter (cm) | 12 cm | 6 cm | 12 cm |
| Cross Sectional Area (cm2) | 123 cm2 | 341.4 cm2 | 123 cm2 |
| Particle size | 45-165 um | 45-165 um | 45-165 um |
| Linear Velocity | 400-700 cm/hr | Not applicable | 400-700 cm/hr |
| Max Pressure | 2 bar | 2 bar | 2 bar |
| Operating Pressure | 2 bar | <0.5 bar | <0.5 bar |
| Flow Rate | 49-86 L/Hr | 2 L/(0.05 hr) = 39 L/hr 650 mL/min | 49-86 L/Hr |
| Vol Resin Required | 5.1 L | 0.5 L | 5.1 L |
| Dynamic Resin Capacity g Protein/g resin | 120 mg/mL BSA | 120 mg/mL BSA | 120 mg/mL BSA |
| Capacity/column | 610 gm | 240 gm | 610 gm/pass |
| Cycle Time/Batch | 0.9 hr | 2.1 hr | 0.3 hr |
| Batches to purify 2000 L @ 1 g/L | 3.3 | 1 | 3.3 passes |
| Time to purify 2000 L @ 1 g/L (2 Kg) | 3.3 batches × 0.9 hr/batch = 3 hrs | 2.1 hr | 0.3 hr |

A comparison of the processing time required by conventional column chromatography and the disclosed device's processes using the same amount of resin could also be shown. In this case, the disclosed device can be as much as ten times more productive than conventional column chromatography. The magnitude of the productivity increase using the disclosed device can be primarily due to two factors. First, simultaneous washes occur in the disclosed device, allowing all washing and elution steps to proceed concurrently. Second, the disclosed device can have an increase in the rate of mass transfer due to convective mixing as opposed to diffusive mixing in conventional column chromatography as described supra.

In some embodiments, the module 70 containing a mixing apparatus e.g., a rotatable screw 80 contains a chromatography resin. The resin can be transported from entry in the module 70 at the proximal end 72 by rotation of screw 80 along the length of module 70 and at the distal end 74 of module 70 the resin can be striped of tightly bound, non-eluted sample load impurities by addition of strip solution via port 120 and waste strip solution can be drawn out of module 70 at exit port 121. The subsequent addition of equilibration buffer via port 60 re-equilibrates the resin. The equilibration buffer can contain a high salt concentration and thus, about 60% to about 85% of the used equilibration buffer can be removed from re-equilibrated resin in module 70 via exit port 61. The re-equilibrated resin can be returned to recycled resin entrance port 202 through return tubing 102 and being propelled by resin recycle pump 110. Buffer solutions having different functions and compositions can be added and removed, typically equilibration, load, wash, elution, and strip buffer solutions. At various points along cylindrical module 70, an appropriate buffer solution can be added through a port, e.g., 20, to wash impurities from the resin. The impurities plus wash can be removed distal from the addition port 20, at port 21. A screen (not shown) covers each exit port, permitting removal of buffer solution but preventing resin from being removed. This configuration can allow the resin to be continuously equilibrated, loaded, washed, eluted, stripped and re-circulated to proximal end 72 to be re-introduced at input port 202 for reuse. Thus, product can be continuously processed with a reduced amount of resin and less volume of buffer solutions than required in conventional column chromatography.

The rate of transport of the resin divided by the volume of the device is the residence time. In conventional column chromatography, the resin bed can be static and the buffer solutions and sample load solution flow through it. Therefore, the contact time of the resin and buffer would be controlled by the buffer solution flow rate, which would be limited by the pressure generated of the buffer solution flowing through the resin bed. Advantageously, with the disclosed device, the buffer solution flow rate (buffer residence time) and the resin flow rate (resin residence time) can be independently controlled. This enables the operator to optimize the amount of buffer solution needed as well as the rate of processing depending on the kinetics of binding to the resin by the product and associated impurities and product elution.

The amount of resin required to purify a product by column chromatography depends on the capacity of the resin. The capacity to bind product can be determined by the density of product binding ligands. The use of smaller resin particles typically results in a higher concentration of ligands and thus a higher binding capacity of the resin. Unfortunately, smaller resin particles generate higher back pressures. However, in the disclosed system, smaller resin particles can be employed with minimal effect on back pressure.

Resin Recycling:

In another embodiment of the invention, the rate of binding of product and resin, whether it is an affinity binding reaction or not, can be accelerated by injecting newly equilibrated resin into the product binding portion 710 (see FIG. 7) via port 130 of module 70. The binding rate can be described by equation 1 below:

$$dp/dt = (k) \times [\text{Resin Free Binding sites}] \times [\text{Unbound Product}] \quad \text{Equation 2: Rate of Product Binding or } dp/dt$$

Where:
k represents the second order kinetic constant
dp/dt represents the rate of product binding to resin
[Resin Binding sites] represents the concentration of unoccupied ligand binding sites on the resin
[Unbound Product] represents the concentration of unbound product in the load Further product separation, processing and formulation/buffer exchange can also be achieved by controlling the convective mixing of product and resin and so product binding to resin.

Figure 3:
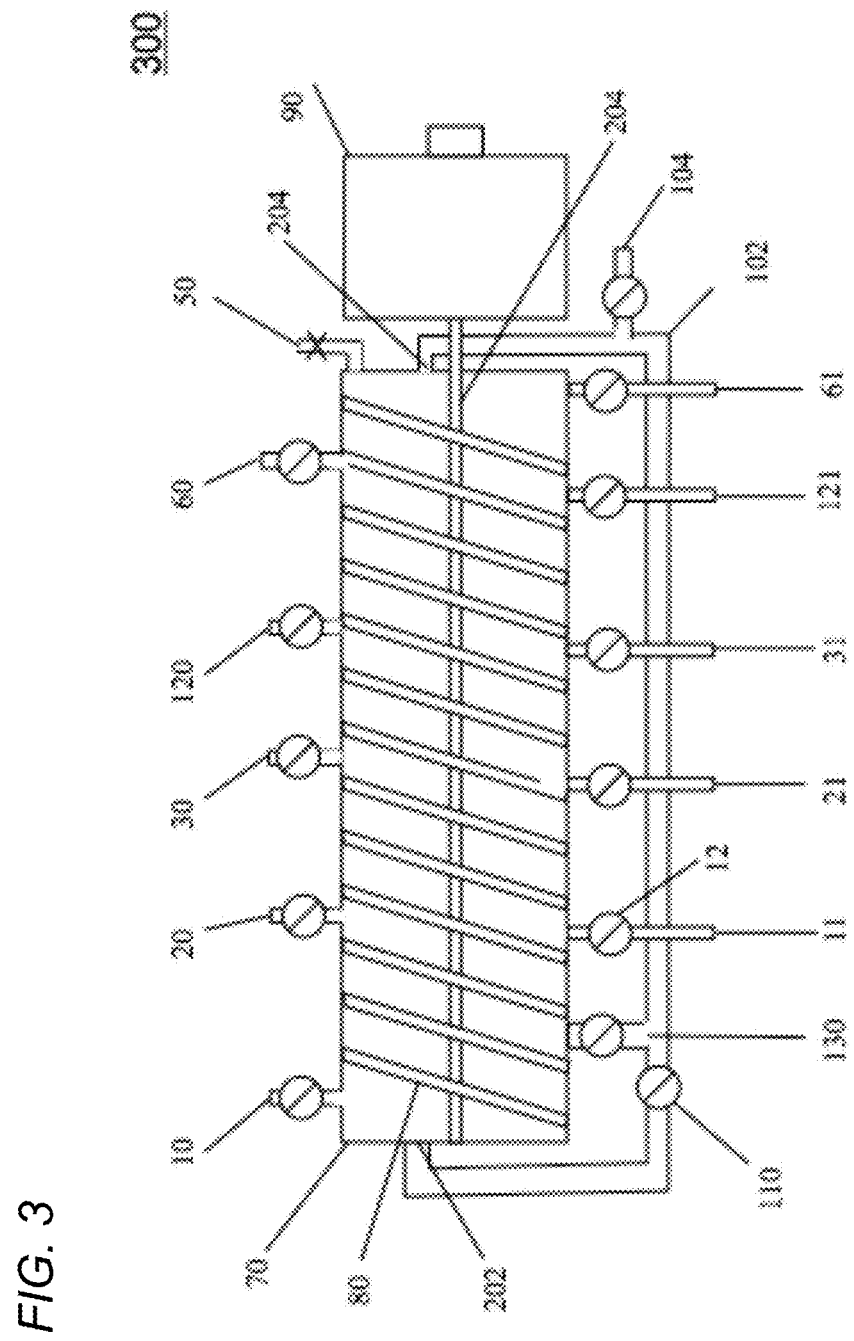
FIG. 3 illustrates one embodiment for replenishing and/or recycling of resin within the disclosed device.

In another embodiment, as illustrated in FIG. 3, the disclosed device can further have a port 130 to inject freshly equilibrated resin, thus increasing the rate of product binding. In this embodiment, the product can move laterally, proximal to distal (e.g., left to right, as illustrated) along device 300 from addition port 10 and new product load can be adsorbed onto the resin and so occupying product binding sites. As the binding sites become occupied, the product concentration in the liquid declines, and the rate of binding of product to resin decreases. While not wishing to be bound by any theory, it appears that injection of freshly equilibrated resin in the Sample Load & Binding Zone 710 (illustrated in FIG. 7), the binding to product can be further increased due to additional available resin binding sites for product binding and therefore, can increase the rate of product binding.

The ability of the disclosed device to continuously recycle resin significantly reduces resin requirements. In a conventional chromatography, a column is designed to bind the maximal amount of product in a single pass. The column is then re-equilibrated and prepared for the next volume of crude material. In contrast, the disclosed device can continuously bind product, elute product, and resin can be re-equilibrated for the next pass. A system, such as the disclosed device, that can continuously recycle resin substantially reduces resin requirements and manufacturing expenditures.

An example of a saving in manufacturing cost is illustrated by the use of Protein S resin. Protein S resin can be one of the preferred resins for purifying monoclonal antibodies. Protein S resin costs about $10,000/L. The protein S resin in a 50 L column would thus cost approximately $500,000. This resin would be typically validated for as many cycles as possible (for example 200 cycles) to reduce cost per gram of product. However, after clinical manufacture, the resin would be replaced with new resin for commercial manufacturing. Thus, a significant expense would be incurred during clinical manufacturing that cannot be recouped. The disclosed device can be operated with as little as 10% of the usual volume of resin used in column chromatography, due to resin recycling. The cost of Protein S resin can be reduced by 90%, saving $450,000 per product (depending on column size) in clinical manufacturing.

Another manufacturing chromatography method makes use of columns used sequentially to isolate large quantities of product. Interest in methods utilizing continuous purification technology has increased during the last several years. With only one exception, these technologies, referred to as Simulated Moving Bed Chromatography (SMBC), simulate moving bed chromatography and rely on chromatography columns connected in series. As the first column can be loaded, the second column can be washed, the third column can be eluted, etc. The sequential nature of such an automated system results in a continuous stream of product, but relies on packed bed column chromatography and an automated system of multi-way switching valves. Although continuously eluting product, SMBC can be susceptible to many of the limitations of packed bed chromatography columns including sensitivity to column packing, maintenance, complexity, cleaning, and protein resolution. Such systems can only be economical due to the economics of scale regarding the large quantity of processed product recovered.

Figure 4:
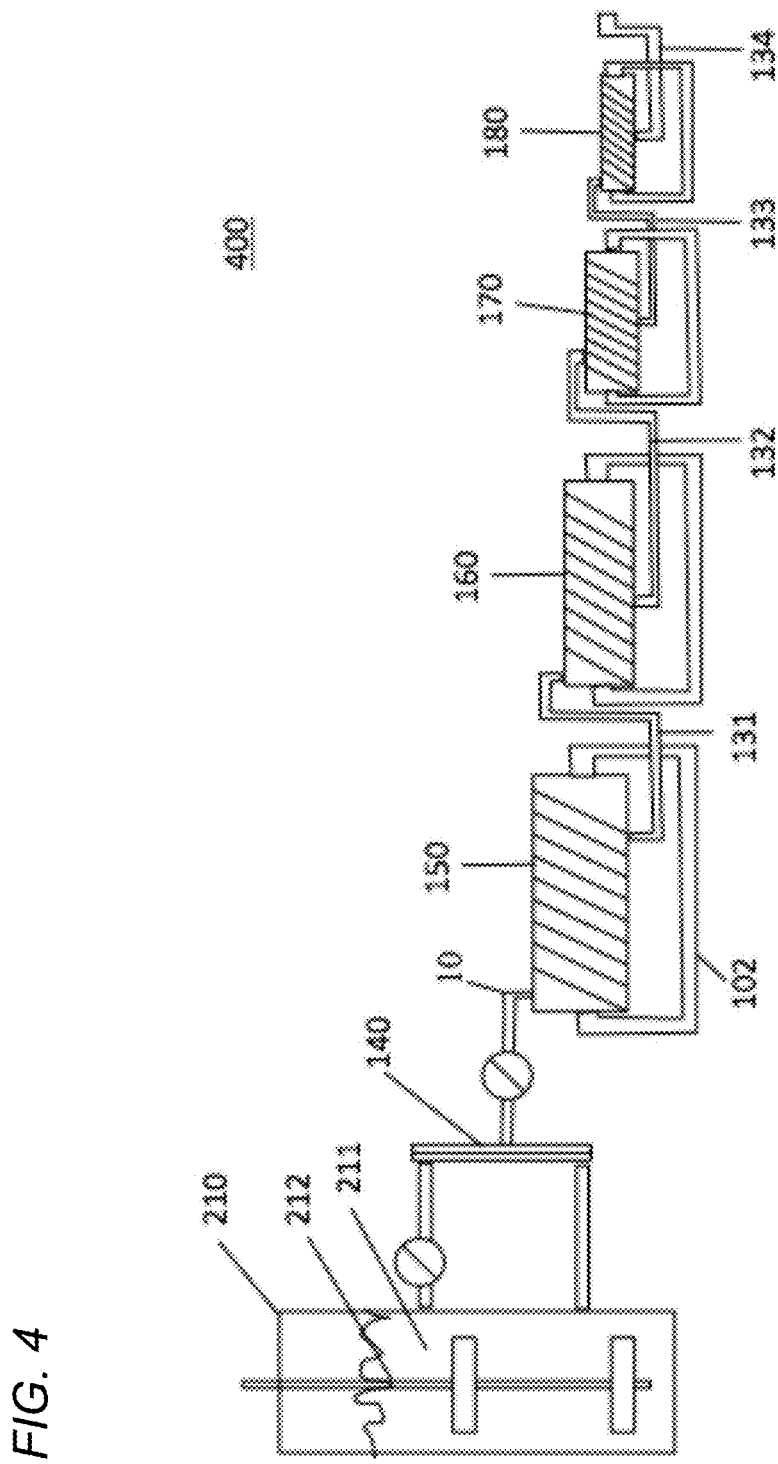
FIG. 4 is a schematic view of one embodiment in which a sample to be processed can be generated and connected in series to a plurality of interconnected devices that can operate in a continuous process.

In another embodiment, the disclosed device can be configured to operate with two or more devices used in a contiguous series employing a distinct separation technology in each cylindrical module 70. As illustrated in FIG. 4, four of the disclosed devices can be arranged in series, labeled devices 150, 160, 170, and 180. In series, each device can be configured to purify the product by a different resin chemistry while concurrently providing a complete purification of product output from a continuous feed stock 210, including but not limited to e.g., a bioreactor (illustrated, but not to be construed as limiting) having a propeller 212. In this illustration, the output from a continuously perfused culture 211 can be pumped through a cell sorter filter 140 and into a first disclosed device 150 that captures and processes the product through, for example, a Protein A Affinity exchange resin, and then processed product from module 150 can then be pumped (not shown) through piping 131 into a second disclosed device 160 that processes product by, for example, anion exchange resin. The processed product from module 160 can then be directed through piping 132 to module 170 that processes product by, for example, cation exchange resin. The processed product from module 170 can then be directed through piping 133 to module 180 that processes product, for example, using a hydrophobic interaction resin. The resulting processed product can be collected at outlet port 134. Any sequence of chromatography chemistries, except for size exclusion, can be used to continuously purify a product to an acceptable purity of product as is known to the skilled artisan.

The selection of resin can be dependent on the net charge of the product to be extracted from the sample load solution. Exemplary resins include, but are not limited to, an anion exchange resin, a cation exchange resin, an affinity resin, a hydrophobic interaction resin, and a reverse phase resin. In some embodiments, the resin can be in the form of a solid resin, a porous resin, a ligand coated matrix, and combinations thereof as is known to one of skill in the art.

Figure 5:
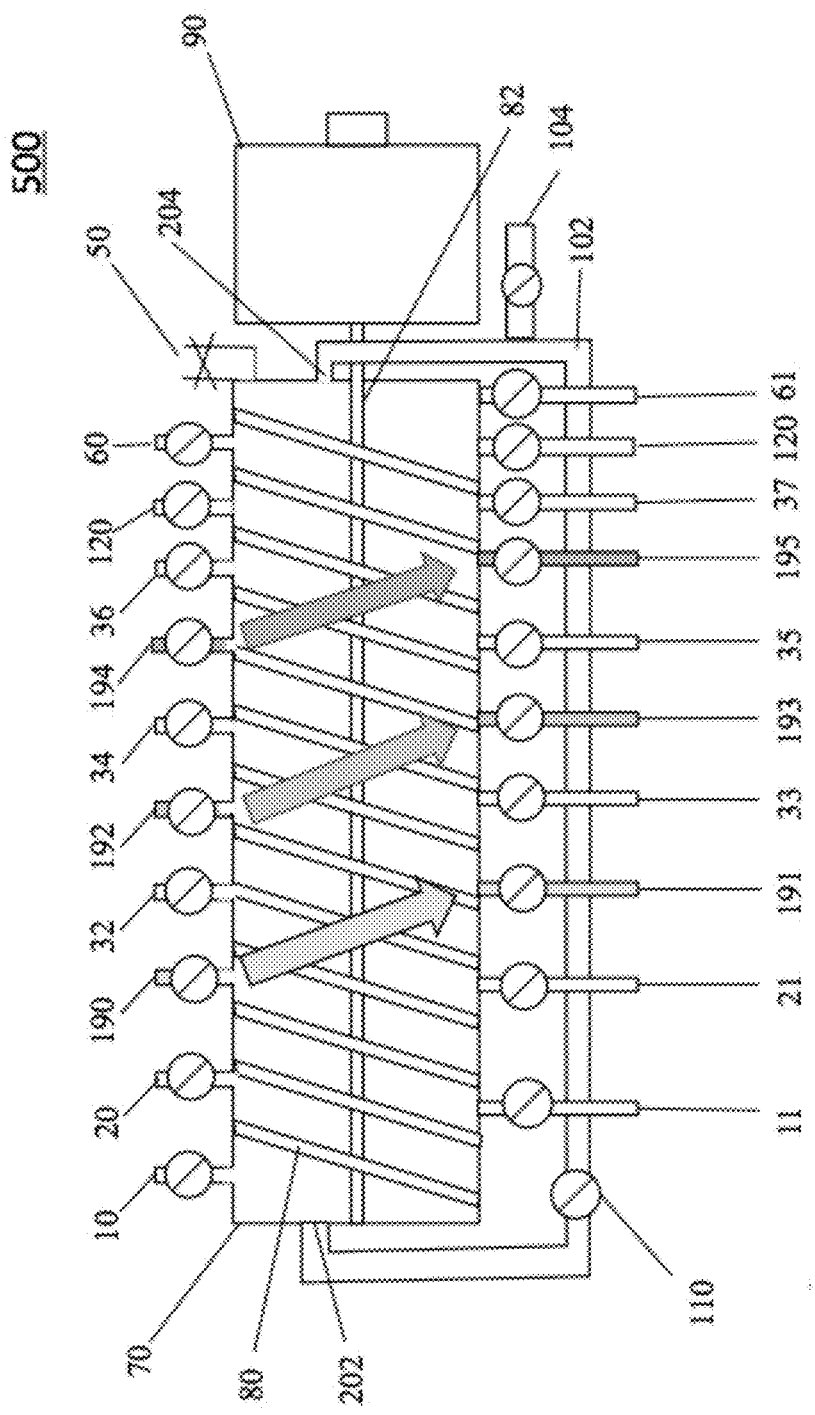
FIG. 5 is a schematic view depicting one embodiment for processing multiple products in succession from a single impure load.

In some embodiments, the disclosed device can be used to separate numerous products from a single feedstock. FIG. 5 illustrates device 500 which can be configured to purify multiple products from a single impure load (not shown). For example, this configuration could be used to process multiple blood factors (e.g., two factors and a protein fraction can be illustrated: FVIII, FIX and HSA, though configurations to elute fewer or more factors can be envisioned) from a plasma pool. The sample load solution can be added at port 10. Wash buffers of sufficient conductivity can be sequentially added to remove impurities and can be added at ports 20, 32, 34, and 36. These wash buffers can be sufficiently strong to remove impurities, but not so strong that they wash off subsequent processed products. Waste wash solution can be removed from ports 21, 33, 35 and 37. Separate buffers, formulated to elute products with varying and increasingly stronger conductivities can be added at points 190, 192, and 194. The eluted factor products can be collected via ports 191, 193, and 195. Resin can be recycled by first stripping the resin of tightly bound impurities. A strip solution can be added at port 120 and removal of strip solution plus stripped impurities can be extracted at the distal end 74 of device 500 through port 121. The addition of Equilibration buffer at one or more of port(s) 60 re-equilibrates the resin for reuse. At least about 10% of the used re-equilibration buffer can be drawn off module 70 via port 61. The Re-equilibrated resin can be recovered at resin exit port 204 in communication with resin recycle tubing 102. The recycled resin can be returned by pump 110 to the proximal end 72 of device 500 at resin entry port 202. Mixing of resin with sample load, various buffer solutions and buffer solution for resin rejuvenation can be done with a variety of mixing apparatus 80 as is known to one of skill in the art. Illustrated, but not to be construed as limiting, a helical screw 80 can mix and move the resin-buffer solution mixture along devise 500, proximal end 72 to distal end 74 the screw being rotated by variable speed pump 90.

While not wishing to be bound by any theory, the disclosed system's ability to purify product can be described by a function of the amount of free product binding ligands contained in the device and the rotation rate of the screw. Thus, increasing the diameter of the tube and the size of the screw can result in a greater amount of processed product per unit of time and higher convective mass transfer due to higher linear velocities. Likewise, because the resin bed in the disclosed module does not require packing, the size of the device cannot be limited by the difficulties in resin bed packing.

Methods

Extraction and Purification of a Protein Product from a Cell Culture Fluid

FIG. 1 shows one embodiment of the device 100. Equilibrated resin flows into a tube 70 containing a screw 80 and can be propelled down a longitudinal axis shaft 82 by screw 80 rotation controlled by variable speed drive 90. Sample Load solution having product with associated impurities can be added at port 10. Any impurities that do not bind to the resin can be removed by gravity or pump 12 at waste exit port 11. A buffer formulated to remove weakly binding impurities without removing product can be added at input port 20. Wash buffer containing impurities can be removed at port 21. A buffer formulated to elute the product from the resin, elution buffer can be added at port 30. Elution buffer containing the product can be recovered at port 31. A buffer, designated Strip, formulated to remove strongly binding impurities from processed resin can be introduced at port 120 and removed at port 121. A buffer designated Equilibration Buffer can be introduced at port 60 and removed at port 61. After equilibration of the resin it can be removed from module 70 at port 204 which can be in communication with resin recirculation tube 102 which return re-equilibrated resin via pump 110 through resin recirculation tube 102 to resin entrance 202.

Figure 2:
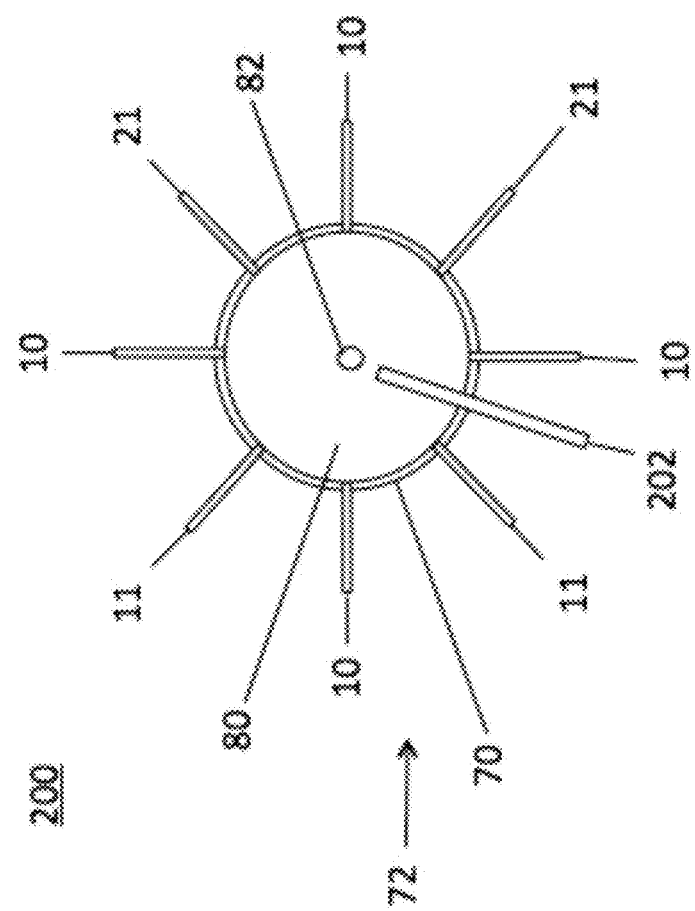
FIG. 2 is an end view of the device of FIG. 1.

FIG. 2: End view 200 of device 100 showing multiple sample load solution addition ports 10, in a first plane and sample load waste exit ports: 11, in a second plane around the circumference of the tube 70 to facilitate thorough contact between buffers and resin. Also shown are screw 80, resin entry port 202, and screw drift shaft 84.

Figure 7:
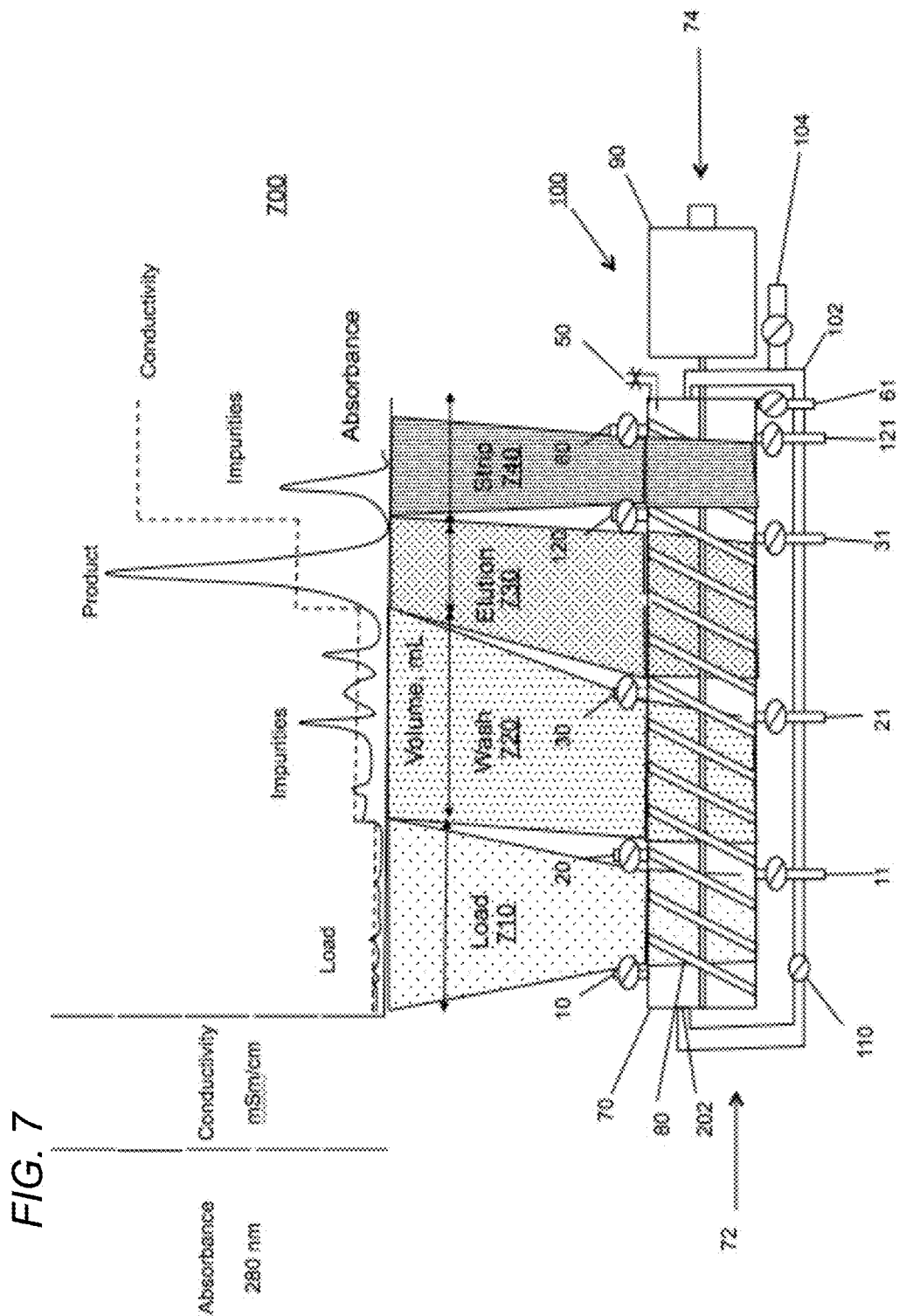
FIG. 7 is a comparison of the results and methods of conventional purification and the invented method used to process a product using a device similar to that of FIG. 1.
Figure 8:
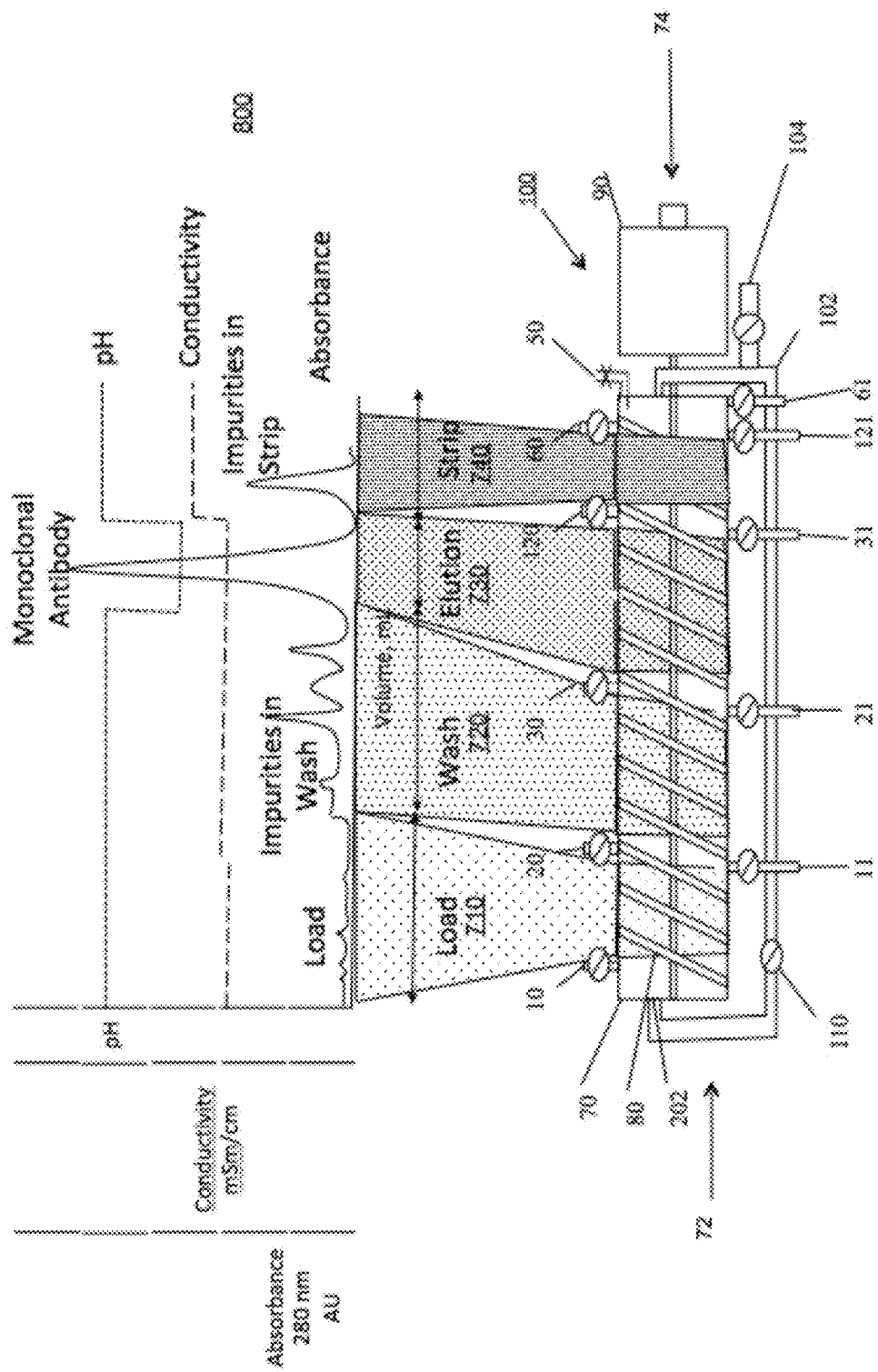
FIG. 8 is a comparison of the results and methods of conventional purification and the invented method used to process a monoclonal antibody product using a device similar to that of FIG. 1.

FIG. 3: This figure illustrates another embodiment of the disclosed device. This embodiment enables freshly equilibrated resin (not shown) to be injected through port 130, thus increasing the rate of product binding to resin. In this embodiment, the product added at inlet port 10 moves down the tube 70 and product can be adsorbed onto product binding sites on and/or within the resin. As the binding sites become occupied, the product concentration in the resin declines, and the rate of binding of product to resin decreases. Injection of freshly equilibrated resin at port 130 in the product load/binding region 710 (not shown) can increase the binding sites available for product to bind to resin and therefore increases the rate of product binding. The resin:product binding, wash, elution and resin:impurities strip zones are depicted in FIG. 7.

FIG. 4: Illustrates four of the disclosed devices each with a different resin chemistry: 150, 160, 170, and 180 configured to purify the product (not shown) and can provide a complete purification of product(s) at the output port (shown??) from a continuous bioreactor 210. In this example, the output from a continuously perfused culture 211 can be pumped into a device 150 that captures the product (not shown) and the resulting product (not shown) purified from unit 150 can be directed into a second unit 160 that purifies product (not shown) by anion ion exchange followed by a cation exchange in a third unit 170, followed by a hydrophobic interaction resin exchange in a fourth unit 180. Any sequence of chromatography chemistries can be used to continuously purify a product, as is known to one of skill in the art.

FIG. 5: Illustration of another embodiment of the disclosed device. In this embodiment the device 500 has been configured to purify multiple products from a single impure load (not shown). For example, this configuration could be used to purify multiple blood factors and fractions (e.g., FVIII, FIX and HSA) from a plasma pool. Separate buffers formulated to elute products with varying and increasingly stronger conductivities can be added at points 190, 192, and 194. Wash buffers of sufficient conductivity can be sequentially added to remove impurities and can be added at points 32, 34, and 36. These wash buffers can be sufficiently strong to remove impurities, but not so strongly that they wash off subsequent products. Buffers of sufficient strength to remove the products can be added at ports 190, 192, and 194. Waste can be removed from ports 33, 35 and 37, products can be collected via ports 191, 193, 195. Equilibrated Resin can be recirculated through 102 by pump 110 to entry port 202 and helical screw 80 can be rotated by variable speed pump 90.

Figure 6:
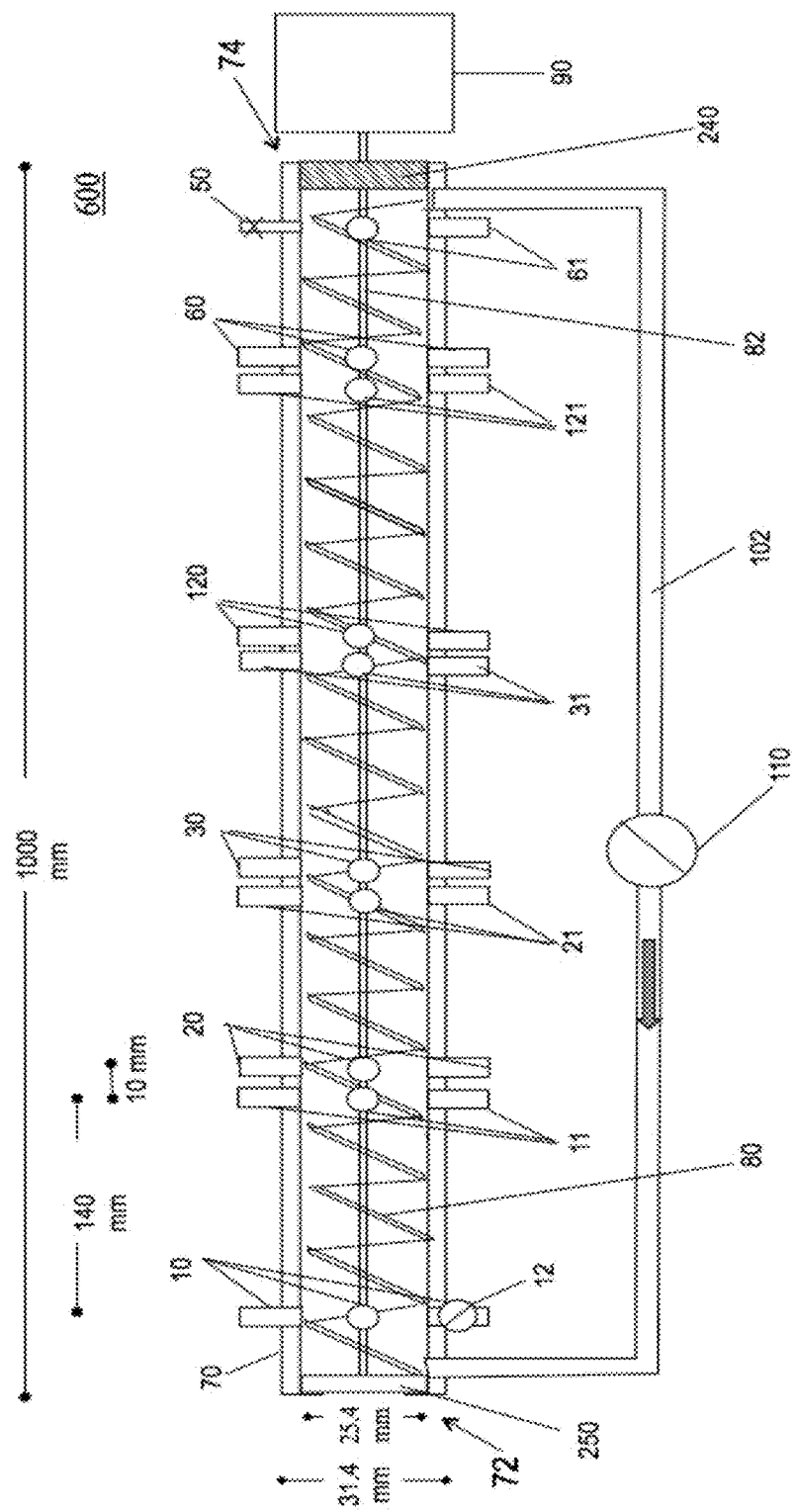
FIG. 6 is an illustration of one embodiment of the disclosed device with approximate sizes, diameters, part locations and length of the disclosed device. Sizes, proportions and components can be illustrative and not to be construed as limiting.

In some embodiments, the disclosed device can be customized to suit the separation, purification and/or formulation/buffer exchange process. FIG. 6 is an illustration of the approximate proportions of a cylindrical module and positions of input ports 10, 20, 30, 120, and 60 and output ports 11, 21, 31, 41, 121, 61. The proximal end 72 has a stopper 250 to retain the resin/sample load buffer solution mixture and a distal end 74 liquid impermeable seal 240 to allow the screw drive shaft 82 that rotates the mixer screw 80 from variable speed drive motor 90. Also depicted are at least three addition ports and at least three exit ports for each buffer solution and waste or elution solution. As illustrate each of the one or more ports can be each arranged in a single plane around the circumference of module 70. One of skill in the art can envision other arrangements, positions and numbers of addition and exit ports, tubing(s), mixing apparatus and pump 12 (not shown with respect to each port).

EXAMPLES

Proteins from Cow's Milk—

Cow's milk contains a complex mixture of proteins and is readily available. It can be used to demonstrate the purification capabilities of the disclosed device. Bovine skim milk can be reduced to pH 4.0 with acetic acid causing some proteins to aggregate. These proteins were removed by centrifugation. The supernatant can be adjusted to pH 7.0 with NaOH, as is known to one of skill in the art. The proteins in this crude protein mixture solution can be processed, separated, and/or analyzed in the following examples.

Example I Protein Purification by Conventional Column Chromatography

First, proteins can be purified by conventional anion exchange chromatography in which the bound proteins were eluted by a gradient of conductivity produced by a sodium chloride solution as is known to one of skill in the art.

A modified lateral rather than vertical chromatography column can be produced from a 25.4 mm interior diameter (ID) cast acrylic cylindrical tube module with a wall diameter of 6.0 mm. A rubber stopper 250 the proximal 72 end of module 70 tube and a hole of 11.00 mm ID can be drilled in each of them. The hole in the distal 72 exit seal 240 can be covered with a nylon screen to prevent the escape of resin particles and resin exit port 201 can be in direct communication with resin recycle tubing 102.

A crude protein mixture can be pumped into the upper stopper/entrance 202 to the module 70 at a rate of 2.0 mL/min using a Watson Marlow model 501U peristaltic pump (Watson-Marlow Fluid Technology Group, Wilmington, Mass.). The surface area can be calculated to measure 506 cm$^2$ and at a flow rate of 2.0 cm$^3$/min equals a linear velocity of 253 cm/min. All solutions can be adjusted to pH 7.0. The resin can be washed with 3 column volumes of NaCl at a conductivity of 2 mSm/cm (milli-Siemens/centimeter), pH 7.0. A linear conductivity gradient of 2 mSm/cm to 500 mSm/cm was applied and the effluent can be monitored at 280 nm as is known to one of skill in the art.

A protein eluting at 20 mSm/cm would be collected.

Example II Protein Purification by the Disclosed Device

The same starting material as will be used in Example I can be purified using the cylindrical module 100 of in the disclosed invention as can be illustrated in FIG. 1 using an elution buffer adjusted to pH 7.0, 20 mSm/cm. Since the conductivity at which the protein elutes will be dependent on its net charge, and the pH of the buffer in which it can be dissolved, affects its net charge, the pH of the solutions can be adjusted to maximize separation efficiency. A protein eluting at 20 mSm/cm can be collected and analyzed by HPLC.

FIG. 7 depicts one embodiment of the disclosed device that can used to process a protein using the disclosed device, e.g., device 100 to produce a processed protein product. Also illustrated will be a graph comparing a chromatogram from a conventional chromatography column (solid line) and of a protein mixture processed using the disclosed devise 100 with conventional column chromatography using conductivity (dashed lines), also referred to as a "step elution". Also illustrated are the projected results for the disclosed device.

To initiate processing of a protein product, a sample load solution can be added to device 100 at the proximal end 72 of device 100 through port 10. The first portion of the chromatogram (solid line) shows the application of the impure product mixture to be processed/purified. This will be referred to as "load". Convective mixing of resin and load (i.e., sample load solution) can occur in region 710. Some impurities flow through the resin, as in conventional column chromatography, and can be removed from device 100 at load waste exit port 11. Mixing in region 710 can also result in other impurities, as well as the product, binding to the resin. In the next phase of the chromatogram a low conductivity e.g., wash buffer (e.g., less then about 20 mSm/cm) can be applied to device 100 at port 20 and the product plus impurities bound to the resin will be washed in region 720. The buffer removes lightly binding impurities, but will not elute the product as described supra. This will be referred to as the "wash". The wash buffer can be removed from device 100 via wash waste port 21. The next portion of the chromatogram shows the application of a higher conductivity elution buffer at elution port 30 that will allow the product to elute. The conductivity will not be so high as to elute tightly binding impurities. This process will occur in the elution region 730. Eluted product material can be collected through elution port 31 and transferred to the product pool (not shown). Only the last part of the conductivity chromatogram (dashed line) shows that the buffer conductivity can be increased by addition of strip buffer solution via port 120. The strip buffer solution will have a substantially greater conductivity, as would be known to one of skill in the art, to "strip" away tightly binding impurities from the resin in strip region 740 which will then be removed from device 100 via strip exit port 121. This waste solution material can be referred to as the "strip".

Resin can then be recycled at the most distal end 74 of device 100 by addition of equilibrium buffer through one or more port(s) 60. The equilibrium buffer will aid in reducing the high conductivity level of the resin after stripping. About 60% to about 85% of the used equilibrium buffer will be withdrawn at the distal end 74 of device 100 through one or more equilibrium exit port(s) 61. Re-equilibrated resin exits the distal end through port 204 in communication with recycle tubing 102 where pump 110 returns the re-equilibrated resin into module 70 via resin entry port 202.

Shading indicates similar functional areas of the invented device.

As can be appreciated by one of skill in the art, the disclosed device can more easily, faster, and economically deliver a processed product.

Example III Human Plasma Fractionation

The disclosed device can also be used to purify blood factors from human plasma. Products such as clotting factors: VIII, IX, V, VII, X, XI, XII, XIII, and vWF and coagulation factors including but not limited to $Rh_o(D)$ immune globulin as well as mammalian plasma serum albumin proteins from human, bovine (including goat and sheep) and porcine sources, fibrinogen, protein globulins selected from alpha 1 globulins, alpha 2 globulins, beta globulins and gamma globulins, and hormone can be currently isolated from human plasma by a combination of ultrafiltration and column chromatography. A less frequently used technique is the Cohn fractionation method that requires multiple organic solvents and cryoprecipitation.

The global plasma fractionation market is estimated to grow at a CAGR of 6.7% from 2016 to 2021 and to reach $26 Billion by 2021. The high cost of recombinant blood factors limits their availability in the third world. Thus, plasma fractionation has become the principle source of these products.

Use of the disclosed device in methods for producing purified plasma products can employ a longer cylindrical module 70, allowing multiple buffers of ever-higher conductivities to be added to the resin in a step-wise elution process. Each protein product can be eluted sequentially at a specific conductivity.

The schematic representation of the disclosed device as it could be configured for plasma fractionation has been illustrated in FIG. 5. Conductivities are not accurate and are for illustration only. In some embodiments, the length of the device can be extended indefinitely to accommodate processing/purification of additional products.

Using device 500 configured to purify multiple e.g., clotting factors from a single impure load (not shown), e.g., blood plasma. For example, this configuration can be used to purify multiple blood factors (e.g., three factors are illustrated: FVIII, FIX and HSA, though configurations to elute fewer or more factors can be envisioned) from a blood plasma pool. The sample load solution, i.e., plasma, will be added at port 10. Wash buffers of sufficient conductivity will be sequentially added to remove impurities and can be added at ports 20, 32, 34, and 36. These wash buffers will be sufficiently strong to remove impurities, but not so strong that they can wash off subsequent products, e.g., factors. Waste wash solution can be removed from ports 33, 35 and 37. Separate buffers, will be formulated to elute factors with varying and increasingly stronger conductivities. The elution solutions will be added at points 190, 192, and 194. Each eluted factor product will be collected via ports 191, 193, and 195.

The result of device 500 being used in a method to purify blood factors FVIII, FIX and HSA provides an efficient, economical and rapid method of supplying blood factors without excessive use of expensive resins. Thus, use of device 500 and variations thereof as disclosed herein and as can be envisioned by the skilled artisan provides unlimited applications for product separation, recovery, and purification. Additionally, the disclosed device can be used in methods to enrich and increase availability of rare and difficult to produce products, biomaterials and the like as would be know to one of skill in the art.

Following elution of each factor the resin can be recycled. Resin rejuvenation will involve a first stripping step in which the resin will be "stripped" of tightly bound impurities. A strip solution can be added at port 120 and removal of strip solution plus removed impurities can be extracted at the distal end 74 of device 500 through port 121. The resin can then undergo re-equilibration by applying a re-equilibration buffer at port 60. About 60% to about 85% of the used equilibration buffer can be removed at port 61. Re-equilibrated resin can be recovered at resin exit port 204 in communication with tubing 102 and resin entry port 104. The re-equilibrated resin can be pumped through tubing 102 by pump 110 and returned to the proximal end 72 of device 500 at resin entry port 202. Mixing of resin with sample load, various buffer solutions and buffer solution for resin rejuvenation can be done using a variety of mixing apparatus 80 as is known to one of skill in the art. Illustrated in FIG. 5, but not to be construed as limiting, can be a helical screw 80. The mixing apparatus can mix resin with sample load as well as move the resin-buffer solution mixture along devise 500 (e.g., from proximal 72 end to distal end 74 of device 500), wherein mixing and movement of resin can be by rotation of helical screw 80 by variable speed pump 90.

Example IV Protein A Purification of Monoclonal Antibodies

Monoclonal antibodies (mAbs) are a significant class of biotherapeutics that are generally produced by mammalian cell culture. Humira®, for example, is the largest selling biotherapeutic ever developed with annual sales exceeding $10,000,000,000. The purification of mAbs is typically accomplished with protein A resin that specifically binds the mAb and allows isolation from the complex mixture of contaminating proteins in the cell culture fluid.

The disclosed device can be used to substantially reduce the amount of protein A resin required per purification cycle. In a typical protein A column used for chromatographic purification, the column can be packed with protein A resin and the HETP and asymmetry can be measured using standard methods. If the column meets predetermined specifications for HETP and asymmetry, the protein A resin can be equilibrated with a mild buffer containing sodium citrate, and sodium chloride, passing approximately three column volumes, at a pH of approximately 6.0. Cell culture fluid can then pass through the column, allowing the product bind to the protein A resin. The concentration of the mAb in the clarified cell culture fluid can be determined by a suitable analytical method, and the volume of crude material loaded can be limited to the total amount of mAb that matches the capacity of the column to bind mAb. The column can be washed with approximately three column volumes of a stronger conductivity buffer, e.g., 20 mM sodium citrate, 1

M sodium chloride, pH 6.0, washing away lightly binding impurities. An elution buffer of 20 mM sodium citrate at approximately pH 3.0 can then be passed through the column causing the product to elute from the resin. The pH of the buffer may be optimized to maximize recovery and minimize aggregation. The processed product would be collected.

Figure 9:
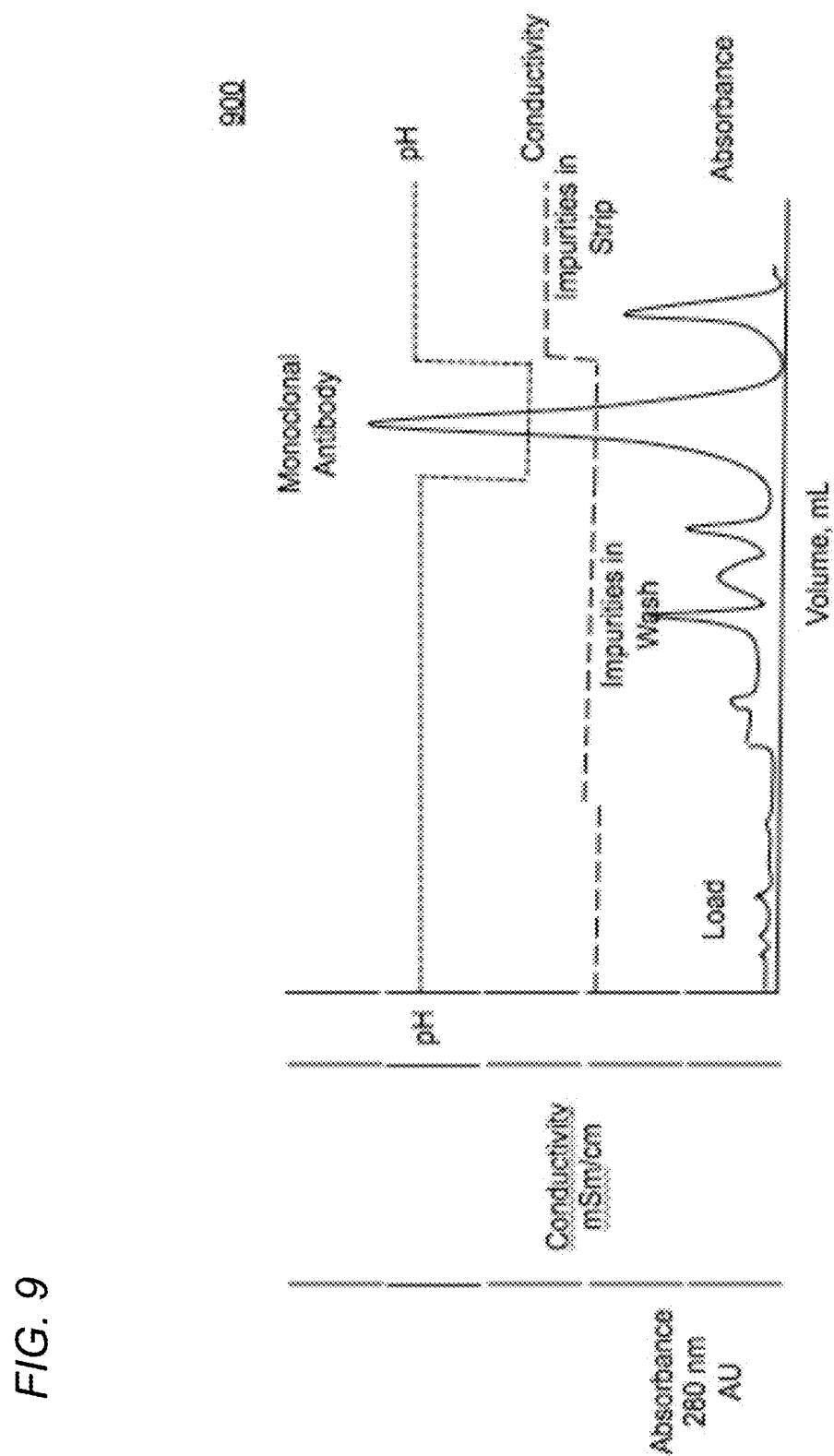
FIG. 9 is a graph illustrating, in one embodiment, an elution profile for elution of e.g., a monoclonal antibody using the disclosed compared to a convention column chromatography elution profile.

In the disclosed device, column packing may not be necessary and thus the assessment of HETP and asymmetry may not be necessary. The equilibration buffer can be formulated to 20 mM sodium citrate, pH 6.0. The load buffer can be unchanged. The wash buffer can be formulated to 20 mM sodium citrate, 1M sodium chloride. The elution buffer can be formulated to 20 mM sodium citrate, pH 3.5. The strip buffer can be formulated to 20 mM sodium citrate, pH 3.0. The pH and conductivities of each buffer would be approximate and can be adjusted to optimize purity and yield of the processed product. The rotation rate of resin passing through the device and the flow rate of the buffers can be adjusted for optimal product recovery and purity. Illustrated in FIG. 8, the disclosed device provides a depiction of the purification of a mAb and the use of pH and conductivity to elute the mAb. FIG. 9 illustrates the elution profile from FIG. 8.

In the event of inconsistent usages between this document and any documents so incorporated by reference, the usage in this document controls.

Each of the non-limiting examples described herein can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

While the principles of this invention have been described in connection with specific embodiments, it should be understood clearly that these descriptions are made only by way of example and are not intended to limit the scope of the invention. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A device, comprising:
   a) a cylindrical module comprising one or more mixing apparatus within the cylindrical module,
   b) a resin, an input port for loading the resin and a tubing in communication with the resin loading input port within the cylindrical module,
   c) one or more air bleed valve(s), wherein the valve extracts accumulated air within the module,
   d) one or more first port(s) for adding a sample load solution and one or more first exit port(s) for removing sample load waste solution essentially absent sample,
   e) optionally, one or more second port(s) for addition of a wash solution and one or more second exit port(s), for removal of wash solution essentially absent sample,
   f) at least one or more elution solution port(s) for addition of an elution solution and at least one or more elution exit port(s) for recovery of the elution solution containing a processed sample,
   g) optionally, one or more additional port(s) for addition of a solution and of one or more additional exit port(s) for removal of the solution, wherein said ports can be used during a single pass through the device at least one or more times to repeat one or both of steps d) and e), wherein the sample load solution comprises two or more samples to be processed,
   h) one or more port(s) for recycling the resin contained within the module comprising:
      i) at least one or more port(s) for addition of a strip solution and at least one or more exit port(s) for removal of the strip solution, wherein sample impurities bound to the resin are removed,
ii) at least one or more port(s) for addition of resin equilibration buffer, wherein stripped resin is re-equilibrated, at least one or more exit port(s) for removing >10% equilibration buffer, and at least one or more exit port(s) for removing re-equilibrated resin, wherein the exit port(s) is in communication with the tubing, and
iii) one or more pumps interconnected to the tubing containing re-equilibrated resin, wherein re-equilibrated resin is recycled into the cylindrical module, and
i) a controller for enabling real time process analytical technology (PAT) control of one or more of buffer, resin flow and mixing rate(s) and analyses of product separation, processing and formulation/buffer exchange.

2. The device of claim 1, wherein the sample load solution is adjusted in conductivity and/or pH, in which impurities within the sample load solution do not bind to the resin and are removed through the one or more first exit ports.

3. The device of claim 1, wherein the mixing apparatus promotes convective mass transfer between the sample load solution and wherein, the resin is circulating.

4. The device of claim 3, wherein adjusting the mixing apparatus by at least one parameter selected from the group consisting of higher RPMs, increase in cylindrical module diameter, increasing one or more of sample load solution, wash solution and/or elution solution flow rates, mechanical projections within the mixing apparatus and combinations thereof to improve convective mass transfer.

5. The device of claim 1, wherein the resin is selected from the group consisting of an anion exchange resin, a cation exchange resin, an affinity resin, a hydrophobic interaction resin, and a reverse phase resin.

6. The device of claim 1, further comprising a pump at each addition port and exit port.

7. The device of claim 1, optionally comprising a resin injection port.

8. A method of using the device of claim 1 to produce a processed product comprising:
a) applying a sample load solution comprising one or more product(s) plus impurities into one or more first port(s), wherein product binds to resin, and removing sample load waste solution via one or more first exit port(s), essentially absent sample,
b) optionally, applying a wash solution via one or more second ports, wherein impurities from the sample solution are removed in wash solution via one or more second exit ports, essentially absent sample, and
c) applying an elution solution to elute product bound to resin via one or more elution ports, wherein the product is a processed product collected via one or more elution exit ports.

9. The method of claim 8, wherein the processed product is selected from the group consisting of a separated product, a purified product, formulation/buffer exchange of compounds, and combinations thereof.

10. A method of using the device of claim 1 for producing two or more products from a single feed stock comprising:
a) applying a sample load solution comprising impurities and two or more products to be processed into one or more first port(s), wherein two or more products substantially bind to resin and removing sample load solution via one or more first exit port(s), essentially absent sample,
b) optionally, applying a wash solution via one or more second port(s), wherein impurities are removed via one or more second exit port(s), essentially absent sample,
c) applying a first elution solution via one or more first elution port(s), wherein a first processed product is eluted from the resin and collected via one or more first elution exit port(s),
d) optionally, repeating step b) before repeating step c) via at least one or more optional wash port(s) and adding a second wash solution to one or more second wash port(s), and
e) repeating step c) via one or more additional elution port(s) wherein a second and each additional processed product is eluted from the resin and collected via one or more additional elution exit port(s) for recovery of the second and each additional processed product(s).

11. The method of claim 10, wherein the feedstock is selected from the group consisting of a compound product sample and a blood product.

12. The method of claim 11, wherein the blood product is plasma.

13. The method of claim 12, wherein recovered from the plasma are at least two proteins selected from coagulation factor(s), plasma protein fraction(s), and combinations thereof.

14. A method of using the device of claim 1 for processing an analyte comprising:
a) applying a crude sample solution comprising an analyte plus impurities into one or more first port(s), wherein analyte binds to resin, and removing crude sample solution via one or more first exit port(s), essentially absent sample,
b) optionally, applying a wash solution to wash analyte bound to resin via one or more second ports, wherein impurities from the crude sample solution are removed via one or more second exit port(s), essentially absent sample,
c) applying an elution solution to elute the analyte from resin via one or more elution ports, wherein processed analyte is collected via one or more elution exit ports,
d) analyzing the processed analyte for purity, and
e) optionally quantifying the analyte.

15. The method of claim 14, wherein one or more of the analysis is selected from the group consisting of conductivity, pH, high-pressure liquid chromatography (HPLC), ultraviolet (UV)/visible (V) spectroscopy, mass spectroscopy (MS), electrophoresis, and capillary electrophoresis (CE).

16. The method of claim 14, wherein the analysis comprises process analytical technology (PAT).

17. The method of claim 16, wherein PAT provides feedback for adjusting a processing parameter selected from the group consisting of mixing apparatus speed, and pump flow rates.

18. The method of claim 16, wherein the PAT utilizes one or more of conductivity, pH, high-pressure liquid chromatography (HPLC), ultraviolet (UV)/visible (V) spectroscopy, mass spectroscopy (MS), electrophoresis, and capillary electrophoresis (CE) testing.

* * * * *